(12) United States Patent
Baker et al.

(10) Patent No.: US 8,920,313 B2
(45) Date of Patent: Dec. 30, 2014

(54) ADJUSTABLE MULTIFUNCTIONAL MEDICAL EXAMINATION INSTRUMENT

(71) Applicants: Jeff Baker, Orlando, FL (US); Michael Deimen, Lindsay, TX (US); Stephanie Lutz Paulauskas, Orlando, FL (US)

(72) Inventors: Jeff Baker, Orlando, FL (US); Michael Deimen, Lindsay, TX (US); Stephanie Lutz Paulauskas, Orlando, FL (US)

(73) Assignee: Promising Ground, LLC, Orlando, FL (US)

( * ) Notice: Subject to any disclaimer, the term of this patent is extended or adjusted under 35 U.S.C. 154(b) by 0 days.

(21) Appl. No.: 13/891,757

(22) Filed: May 10, 2013

(65) Prior Publication Data

US 2014/0039262 A1  Feb. 6, 2014

Related U.S. Application Data

(60) Provisional application No. 61/645,182, filed on May 10, 2012.

(51) Int. Cl.

| | | |
|---|---|---|
| *A61B 1/267* | (2006.01) | |
| *A61B 3/10* | (2006.01) | |
| *A61B 1/00* | (2006.01) | |
| *A61B 1/32* | (2006.01) | |
| *A61B 1/307* | (2006.01) | |
| *A61B 1/06* | (2006.01) | |
| *A61B 1/227* | (2006.01) | |
| *A61B 1/31* | (2006.01) | |
| *A61B 1/303* | (2006.01) | |
| *A61B 1/24* | (2006.01) | |

(52) U.S. Cl.
CPC . *A61B 1/32* (2013.01); *A61B 1/227* (2013.01); *A61B 3/10* (2013.01); *A61B 1/00137* (2013.01); *A61B 1/00101* (2013.01); *A61B 1/31* (2013.01); *A61B 1/307* (2013.01); *A61B 1/303* (2013.01); *A61B 1/00034* (2013.01); *A61B 1/06* (2013.01); *A61B 1/24* (2013.01); *A61B 1/00103* (2013.01); *A61B 1/00082* (2013.01)
USPC .......................................................... 600/200

(58) Field of Classification Search
CPC ........ A61B 1/06; A61B 1/24; A61B 1/00052; A61B 1/227; A61B 1/233; A61B 1/0669
USPC .......................... 600/106, 115, 116, 184–246
See application file for complete search history.

(56) References Cited

U.S. PATENT DOCUMENTS

| | | | | |
|---|---|---|---|---|
| 3,978,850 | A | * | 9/1976 | Moore et al. .................. 600/200 |
| 4,380,998 | A | * | 4/1983 | Kieffer et al. ................. 600/200 |
| 6,383,133 | B1 | * | 5/2002 | Jones ............................. 600/200 |
| 2006/0253087 | A1 | * | 11/2006 | Vlodaver et al. ............. 604/275 |

(Continued)

*Primary Examiner* — Jerry Cumberledge
*Assistant Examiner* — Tessa Matthews
(74) *Attorney, Agent, or Firm* — Timothy H. Van Dyke; Beusse, Wolter, Sanks & Maire, P.A.

(57) ABSTRACT

A speculum configured for attachment to an otoscope attachment of a medical examination instrument is provided in an embodiment herein. The speculum includes a proximate end, a distal end, and a speculum body extending from the proximate end to the distal end. The proximate end is configured for attachment to a first end of the otoscope attachment, and the distal end is configured for penetration into an orfice of a subject. The adjustable speculum further includes at least one flange, wherein the at least one flange is adjustably positioned on the speculum body between the proximate end and the distal end to limit a depth of the penetration of the speculum in the orfice.

13 Claims, 5 Drawing Sheets

(56) References Cited

U.S. PATENT DOCUMENTS

| | | | |
|---|---|---|---|
| 2008/0091081 A1* | 4/2008 | Marino | 600/219 |
| 2009/0112067 A1* | 4/2009 | Baker | 600/199 |
| 2011/0092770 A1* | 4/2011 | Matsui et al. | 600/115 |
| 2011/0190583 A1* | 8/2011 | Ashida et al. | 600/115 |
| 2012/0059224 A1* | 3/2012 | Wellen et al. | 600/200 |
| 2012/0059225 A1* | 3/2012 | Gostout et al. | 600/204 |

* cited by examiner

ADJUSTABLE MULTIFUNCTIONAL MEDICAL EXAMINATION INSTRUMENT

BACKGROUND

The subject matter described herein generally relates to instruments adapted to assist in conducting one or more tasks associated with the course of a medical examination. The instruments provided herein, further present a convenient, economical method to conduct a preliminary medical examination in one's own home. Therefore, with the consistently rising costs of health care and the hassles involved with hospital visits, one benefits from making the most out of an at-home medical examination before seeking professional medical advice. In some instances, a hospital visit may not be necessary once an at-home medical examination has been performed.

Various types of childhood illnesses occur often during a child's life, and can present a financial strain on the guardian of the child. According to the American Chiropractic Association (ACA), 10 million new cases of ear problems in children occur every year (see at: www.acatoday.org/content_css.cfm?CID=69). Ear infections (otitis media) are the most common illness affecting babies and young children and the number one reason for visits to the pediatrician, which accounts for more than 35 percent of all pediatric visits. Almost half of all children will have at least one middle ear infection before they're a year old, and two-thirds of them will have had at least one such infection by age 3. Children are more prone to ear infections because the immune system, which protects the body against infectious organisms, is not yet fully developed in young children. When a baby is born, the immune system is stimulated by the exposure to new germs and begins to produce antibodies. The immune system continues to grow as it is exposed to new germs. However, if a baby is encountering a new germ for the first time, antibodies have not yet formed. As a result, young children are more prone to infections than adults. The symptoms of an ear infection can include ear pain, fever, and irritability. While they occur more often in children, middle ear infections can also occur in adults. Therefore, an early diagnosis of such an infection can prevent unnecessary pain and suffering in a patient.

Ears are made up of several parts, including the outer ear (auricle and ear canal), middle ear, and inner ear. The auricle can be easily damaged as it is skin-covered cartilage with only a thin padding of connective tissue. Therefore, any trauma to the ear can cause enough swelling to jeopardize the blood supply to its framework, i.e., the auricular cartilage. The ear canal can be injured as a result of exposure to firecrackers and other explosives, or as a result of mechanical trauma from placement of foreign bodies into the ear. Like outer ear trauma, middle ear trauma most often comes from blast injuries and insertion of foreign objects into the ear, wherein inner ear trauma is primarily caused by either exposure to elevated sound levels (noise trauma) or by exposure to drugs and other substances (ototoxicity). Because ear trauma can occur with the insertion of foreign object into the ear, the medical instruments used (i.e., otoscopes) to examine ears must be sensitive to the size and shape of the particular ear which is being examined in order to prevent injury. The ear canals of a child and an adult are different; two major differences are the shape and size of each.

External ear development is a lengthy and complex process which extends from early embryonic life until well into the postnatal period. Initial development of the auricle and external auditory canal during the fourth and fifth weeks of gestation is closely associated with anatomical changes involving the pharyngeal arch apparatus of the human embryo. The auricle and external canal are well formed by the time of birth but do not attain their full size and adult configuration until about 9 years of age. The newborn canal is relatively straight and is considerably shorter and narrower than the canal of an adult. The length of the newborn canal ranges from 13 to 22 mm and the average diameter of the canal is approximately 4.5 mm. In an adult, the ear canal has an S shape. Adult canals have a length of approximately 30 mm and a diameter of approximately 10 mm. Volume of the ear canal is larger in boys than in girls, and the volume is greater in the right ear than in the left ear. The volume of the ear canal of a toddler is between 0.2 and 1.0 ml. The volume of the ear canal of an adult is between 0.9 and 2.0 ml.

The composition of the ear canal changes as the child grows, with the most dramatic growth of the ear canal in the first year. In the newborn, the canal wall is surrounded by elastic cartilage. This causes the newborn canal to be very flexible, yet delicate. Because it is flexible, it is easier to insert a foreign object (specula) too deep into the canal. As the ossicular bone density in newborns is low, the ear canal is more prone to trauma. Once the child reaches approximately four months of age, the canal ossifies and bone has grown around much of the canal. In the adult, only the most lateral third of the canal wall is composed of elastic cartilage, while the medial two-thirds of the canal are encompassed by temporal bone.

Due to the delicacy of the ear as an organ as well as the potential for injury, any contact with the ear must be carefully undertaken and differences in the size, shape, and composition of the ear during the various stages of life must be considered.

BRIEF DESCRIPTION OF THE DRAWINGS

FIG. 5*a* provides the bulb speculum in an extended position, and FIG. 5*b* provides the bulb speculum in a retracted position.

DETAILED DESCRIPTION

Figure 1:
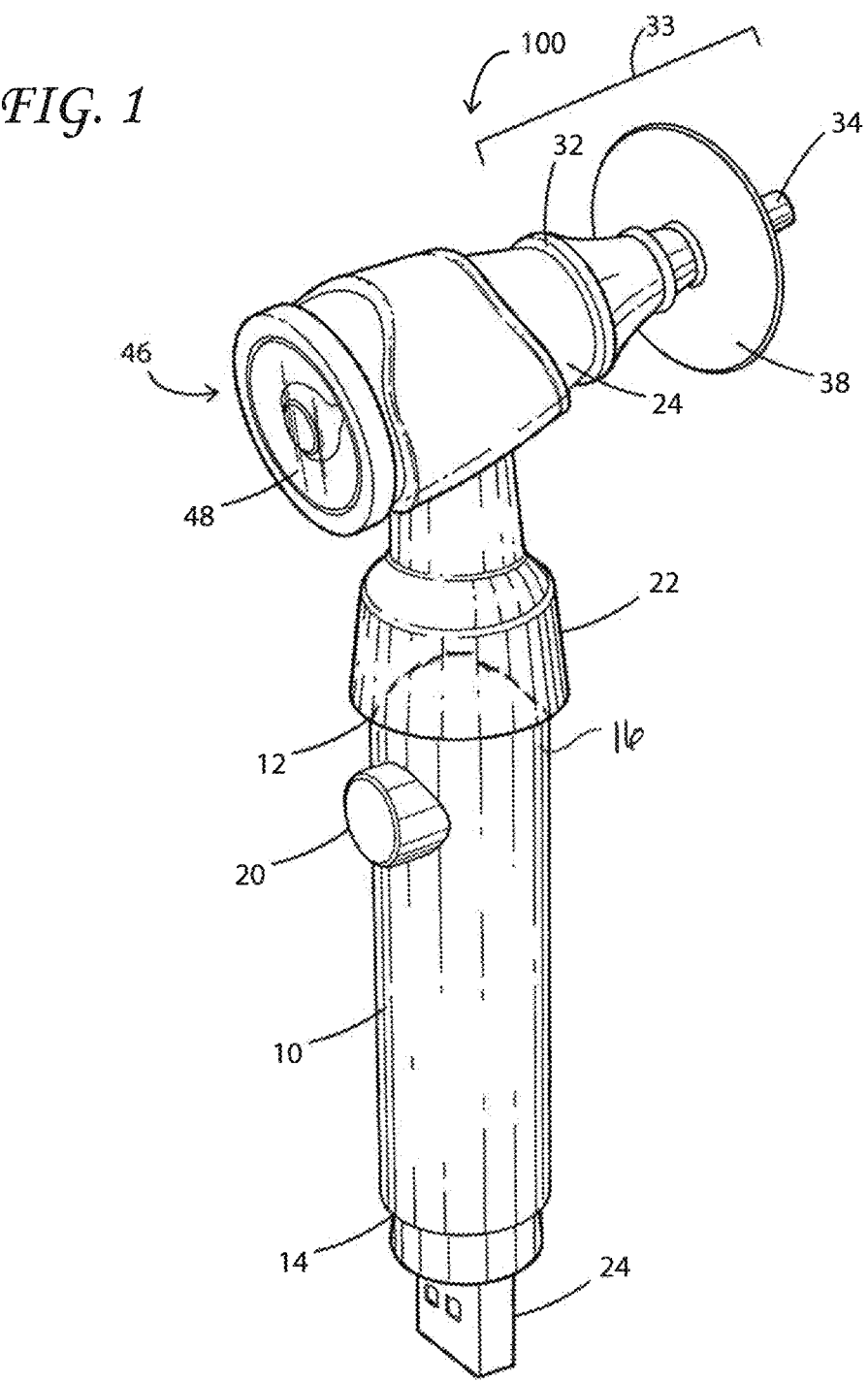
FIG. 1 provides a perspective view of the multifunctional medical examination instrument.

For the purposes of promoting an understanding of the principles and operation of the invention, reference will now be made to the embodiments illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to those skilled in the art to which the invention pertains.

The inventors have identified a need for a convenient and cost-effective means to assist in recognition and evaluation of some of the most common illnesses, particularly childhood illnesses. Such common illnesses include but are not limited to swimmers ear, ear infections, bug bites, skin irritations, etc. By equipping guardians with the instruments needed to evaluate these common ailments, the health issues of the children would be monitored more easily, and perhaps treated more efficiently. The ease of use associated with embodiments disclosed herein, in addition to the cost savings to a user of the embodiments herein, are some of the many benefits of the subject matter described.

In one embodiment, a multifunctional medical examination instrument is provided, said instrument includes an elongated body having a first end and a second end, a light emitting member disposed at said first end of the elongated body, a rechargeable power supply disposed within said elongated body, wherein the rechargeable power supply is in electrical communication with said light emitting member. The instrument further includes an I/O connector projecting out of the second end of said elongated body, the I/O connector in electrical communication with the rechargeable power supply and adapted for operative connection with an external power supply, so as to charge the rechargeable power supply. The instrument further includes an otoscope attachment selectively connectable via an otoscope base fitting to the first end of the elongated body over the light emitting member. The otoscope attachment includes a first end and a second end, wherein the second end comprises a viewing end including a magnifying lens, a mirror disposed in the otoscope attachment to reflect light form the light emitting member through the magnifying lens in the viewing end. The instrument also includes an adjustable speculum removably attached to the first end of the otoscope attachment.

In a further embodiment, the adjustable speculum is provided, including a proximate end and a distal end, wherein the proximate end is configured to attach to the first end of the otoscope attachment, and the distal end is configured for penetration into an orfice of a subject. The speculum further includes a speculum body extending between the proximal and distal ends, and a flange disposed on the speculum body, wherein the flange limits the penetration of the distal end of the speculum into the orfice and provides adjustability of the operable length of the speculum.

In a still a further embodiment, the adjustable speculum is provided wherein a position of the flange on the speculum body is adjustable such that the flange may be positioned at any point along the speculum body between the proximate and the distal end.

In yet a further embodiment, the adjustable speculum is provided wherein the speculum body includes at least one notch disposed thereon, and wherein the flange is positioned within the at least one notch.

In still a further embodiment, the adjustable speculum is provided wherein the speculum ranges from 2 to 5 centimeters in length.

In another embodiment, the adjustable speculum is provided wherein the flange is fixed at a predetermined position on the speculum body. In a further embodiment, the predetermined position is based on the depth of the orfice of the subject.

In another embodiment, the examination instrument is provided wherein the adjustable speculum comprises a proximate end, a distal end, and a speculum body extending from the proximate end to the distal end, the proximate end is configured to attach to the first end of the otoscope attachment, and the distal end is configured for penetration into an orfice of a subject. The speculum is formed of a flexible material and further includes a dial disposed at the proximal end. The dial is adapted to adjust a length of the speculum, such that when the dial is turned in a first direction, the proximate end moves toward the distal end of the speculum and the speculum body forms a bulb shape. When the dial is turned in a second direction, the proximate end moves away from the distal end and the bulb shape is suppressed. The first direction may be a clockwise direction and the second direction may be a counter clockwise direction, or vice versa.

In another embodiment, the orfice comprises a nostril, an eye, an oral canal, an aural canal, an anus, a urethra, a vagina, or a navel.

Another embodiment provides an adjustable speculum configured for attachment to an otoscope attachment of a medical examination instrument. The adjustable speculum includes a proximate end, a distal end, and a speculum body extending from said proximate end to said distal end. The proximate end is configured for attachment to a first end of the otoscope attachment, and the distal end is configured for penetration into an orfice of a subject. The adjustable speculum further includes at least one flange. The at least one flange is disposed on the speculum body between the proximate end and the distal end, wherein the flange limits the depth of penetration of the speculum within the orfice.

In an embodiment, the adjustable speculum is provided wherein the length of the speculum body ranges from 2 to 5 centimeters.

In another embodiment, the adjustable speculum is provided wherein the speculum body further includes at least one notch, and wherein the flange is removably placed within the at least one notch.

In another embodiment, an otoscope kit is provided, the kit includes an elongated body having a first end and a second end; a light emitting member is disposed at the first end of the elongated body. The otoscope kit further includes a rechargeable power supply disposed within the elongated body. The rechargeable power supply is in electrical communication with the light emitting member. An I/O connector is provided projecting out of the second end of the elongated body, the I/O connector is in electrical communication with the rechargeable power supply and adapted for operative connection with an external power supply, so as to charge said rechargeable power supply. The otoscope kit further includes an otoscope attachment selectively connectable via an otoscope base fitting to the first end of the elongated body over the light emitting member. The otoscope attachment includes a first end and a second end, wherein the second end comprises a viewing end comprising a magnifying lens, a mirror disposed in the otoscope attachment to reflect light form said light emitting member through said magnifying lens in said viewing end, and at least one adjustable speculum for attaching to the first end of the otoscope attachment. In a further embodiment, the at least one adjustable speculum is disposable.

In yet a further embodiment, the otoscope kit is provided wherein the at least one adjustable speculum includes a proximate end and a distal end, the proximate end is configured to attach to the first end of the otoscope attachment, and said distal end is configured for penetration into an orfice of a subject. The speculum further includes a speculum body extending between the proximal and distal ends, and a flange disposed on the speculum body, wherein the flange limits the penetration of the distal end of the speculum into the orfice and provides adjustability of the operable length of the speculum.

In still a further embodiment, the otoscope kit is provided wherein the position of the flange on the speculum body is adjustable such that the speculum may be positioned at any point along the speculum body between the proximate and the distal end.

In yet another embodiment, the otoscope kit is provided wherein the speculum body includes at least one notch disposed thereon, wherein said flange is removably placed in the at least one notch.

In still a further embodiment, the speculum ranges from 2 to 5 centimeters in length. In yet a further embodiment, the flange is fixed at a predetermined position on the speculum.

In yet a further embodiment, a speculum configured for attachment to an otoscope is provided, wherein the speculum includes a proximate end for attachment to the otoscope, a speculum body, and a tapered distal end for penetration into an ear of a subject. The speculum further includes a flange positioned on the speculum body to control a depth of the penetration of the speculum into the ear of the subject.

Turning to the Figures, FIG. 1 provides a perspective view of the multifunctional medical examination instrument 100, wherein the elongated body 10 has a first end 12 and a second end 14. The I/O connector 24 can be seen as projecting from the second end 14 of the elongated body 10, and in the embodiment shown the I/O connector 24 is a USB connector. The USB connector can be connected to an external power supply so as to charge the rechargeable power supply which is in electrical communication with the I/O connector. The instrument 100 may also include a cap selectively connectable to the second end 14 of the elongated body 10 to protect the USB connector. An actuator 20 is mounted to the on the elongated body 10 for controlling the operation of the light emitting member 16. The actuator may be embodied as a push button switch or any other type of actuator that is known in the art.

An otoscope attachment 24 is selectively connectable via an otoscope base fitting 22 to the first end 12 of the elongated body 10 over the light emitting member 16. The otoscope attachment includes a viewing end 46 including a magnifying lens 48, a mirror disposed in the otoscope attachment to reflect light from the light emitting member through the magnifying lens in the viewing end 46. An adjustable speculum 30 is removably attached to the first end 12 of the otoscope attachment 24. The adjustable speculum 30 includes a proximate end 32 and a distal end 34, wherein the proximate end 32 is of a size and shape configured to removably attach to the first end 12 of the otoscope attachment 24.

Figure 2:
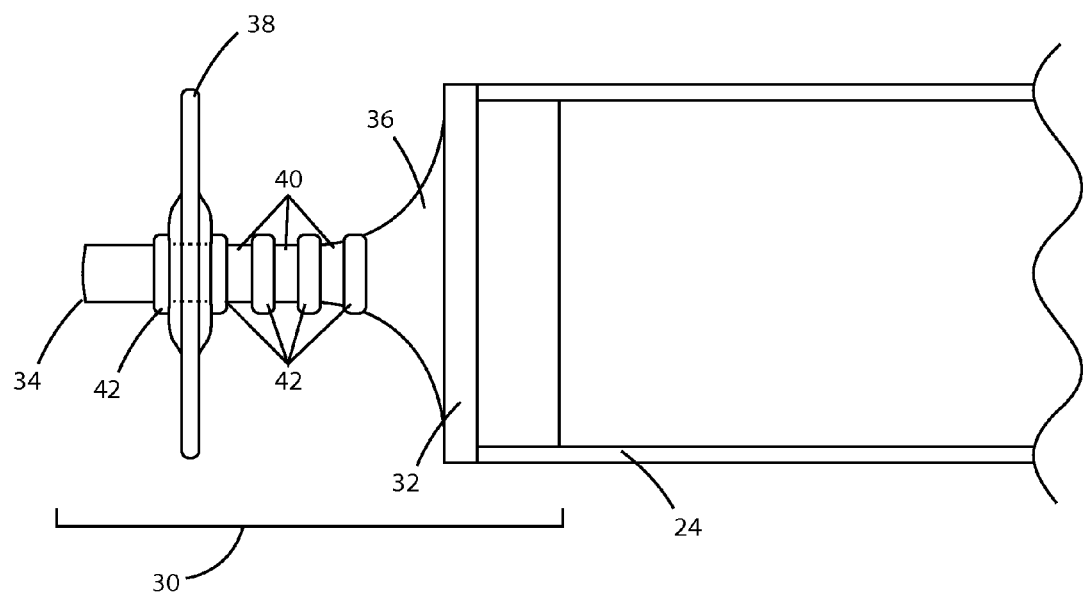
FIG. 2 provides a side view of a speculum.

FIG. 2 provides a side view of a speculum 30 comprising a proximate end 32 and a distal end 34, and a speculum body 36. In the embodiment shown, the speculum body includes four notches 40, and a flange 38 situated within the most distal notch 40. The flange 38, however, may be placed in any of the notches 40 shown. The notches 40 and bumpers 42 provide adjustability of the positioning of the flange 38 along the speculum body 36 between the proximate end 32 and the distal end 34 of the speculum 30. Therefore, the depth of penetration of the speculum 30 in the subject can be controlled by movement of the flange 38 from one notch 40 to another.

The speculum is further provided in FIG. 2, wherein the notches 40 include markings such that a user of the instrument can identify the notch 40 that correlates with a particular age of the subject. The notches 40 are marked by age group, in this embodiment the age groups include "0-1" years of age, "1-4" years of age, "4-18" years of age, and "18+" years of age. As can be seen in FIG. 2, each marking corresponds to an age group of subjects, such that when the flange is placed within the notch, the speculum penetrates the orfice of the subject to the desired degree to provide effective examination and to prevent injury to the orfice. When the speculum is inserted into the orfice to the desired depth, the flange rests on the outer portion of the body of the subject which surrounds the orfice.

Figure 3A:
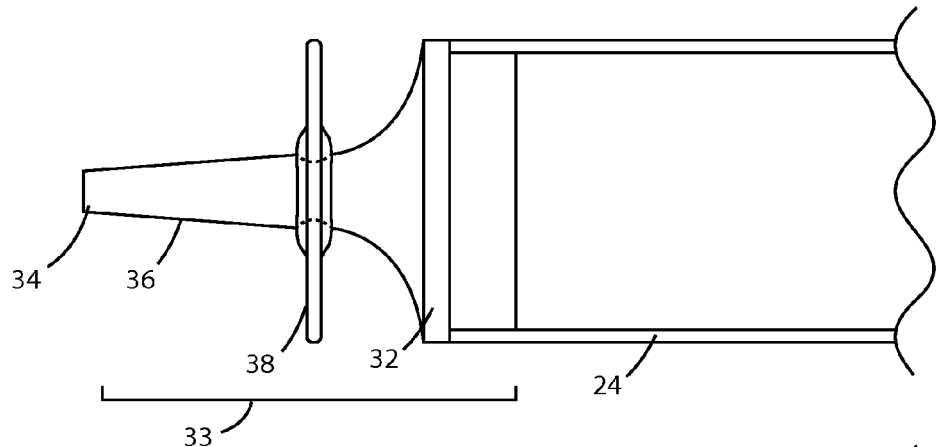
FIGS. 3*a-c* provide side views of fixed speculums of varying lengths.
Figure 3B:
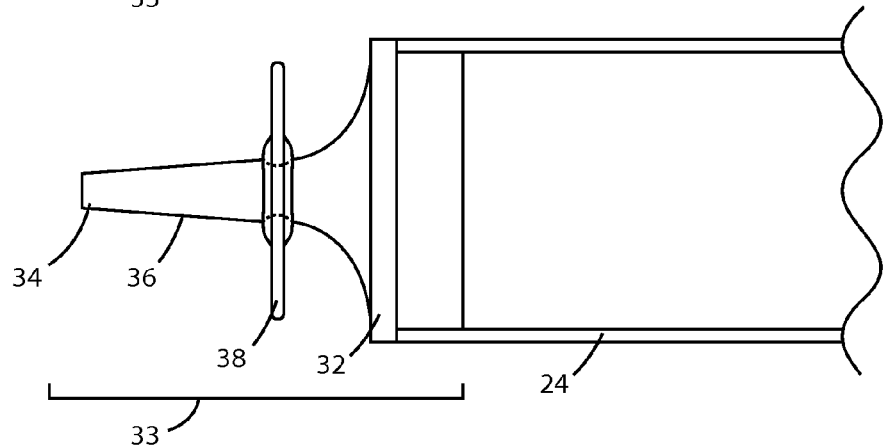
Figure 3C:
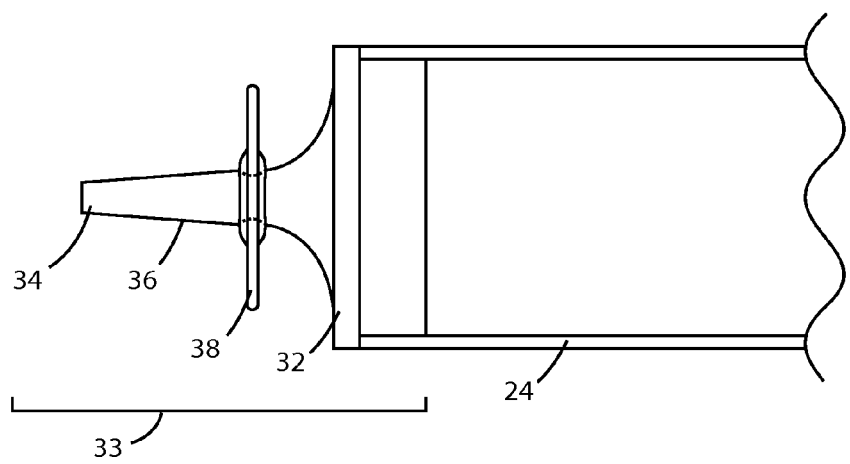

FIGS. 3a-c provide a side view of a fixed speculum 33, wherein the flange 38 is fixed at a predetermined position along the speculum body 36. The sizes of the speculum range between FIGS. 3a-c.

Figure 4:
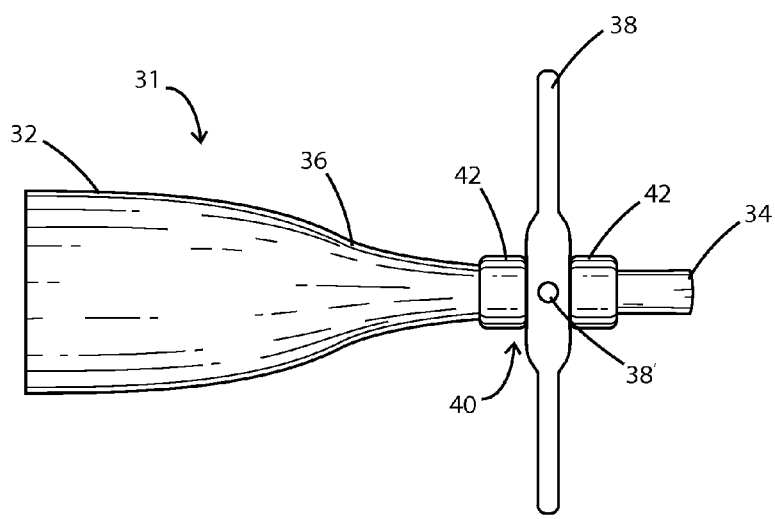
FIG. 4 provides a side view of an adjustable speculum.

FIG. 4 provides a side view of an adjustable speculum 31. The flange 38 may be engaged along the speculum body 36. An actuator 38' is shown, which controls movement of the flange 38 up and down the speculum body. The actuator 38' may have two modes, lock or unlock. In the unlock mode, the flange 38 can slide, in lock mode, the flange 38 is secured. Further shown are two bumpers 42 are positioned on either side of a notch 40, within which a flange is placed 38 along the speculum body 36. The bumpers 42 and notch 40 are optional features that can provide further stability.

Figure 5A:
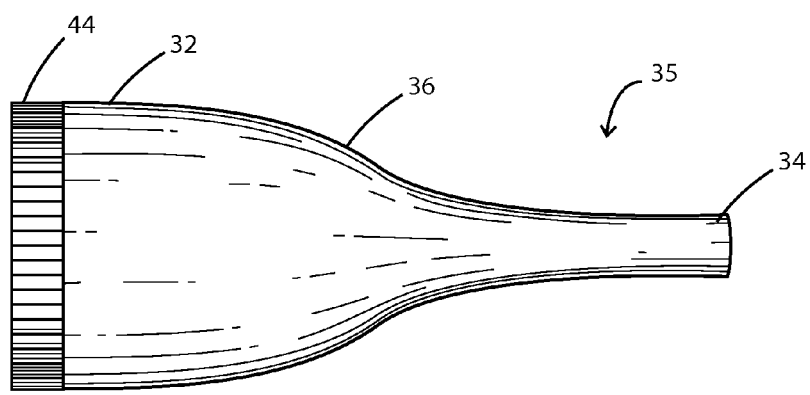
FIGS. 5*a-b* provides a side view of a bulb speculum.
Figure 5B:
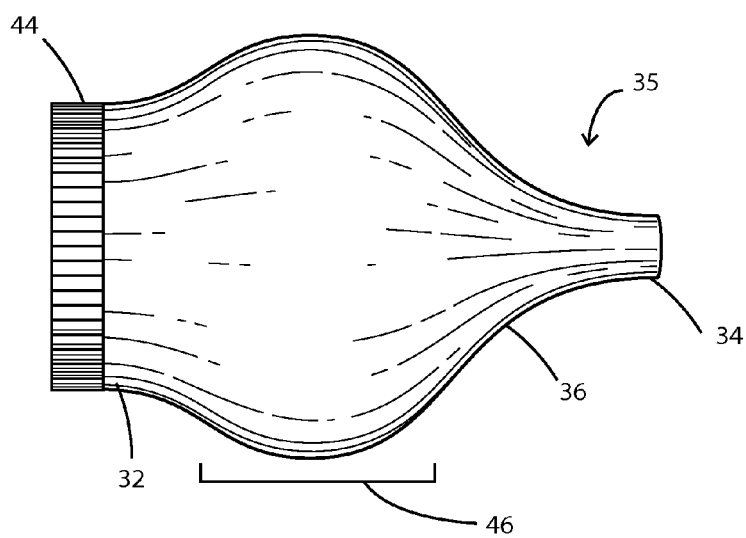

FIG. 5a-b provides a side view of a bulb speculum 35 comprising a proximate end 32 and a distal end 34. A dial 44 is disposed on the proximal end of the bulb speculum as shown, however it may be disposed at any point along the speculum body, or in a different location of the medical examination instrument 100. The dial 44 can be manipulated by a user by turning it in a clockwise or counter clockwise direction. When the dial is turned in a first direction, the speculum body forms a bulb shape, and the distal end 34 nears the proximate end 32 of the speculum 35. When the dial is turned in a second direction, the speculum returns to its original configuration and the bulb shape is removed. The bulb speculum 35 provides a manner of shortening and lengthening the size of the speculum for use in a subject. The embodiment described herein, however, is not limited to use with a dial 44, but may be used with any other device known in the art to produce the same or a similar result. Such devices may include, but are not limited to, a ring that is moved toward the distal end 34 of the speculum to lengthen the speculum body 36, and away from the distal end 34 of the speculum to shorten the speculum body 36, wherein the ring is connected to the distal end 34 of the speculum body 36, and the ring is manipulated prior to, during, or following use of the medical examination instrument 100. Other similar devices may be used to accomplish a similar result.

Figure 6A:
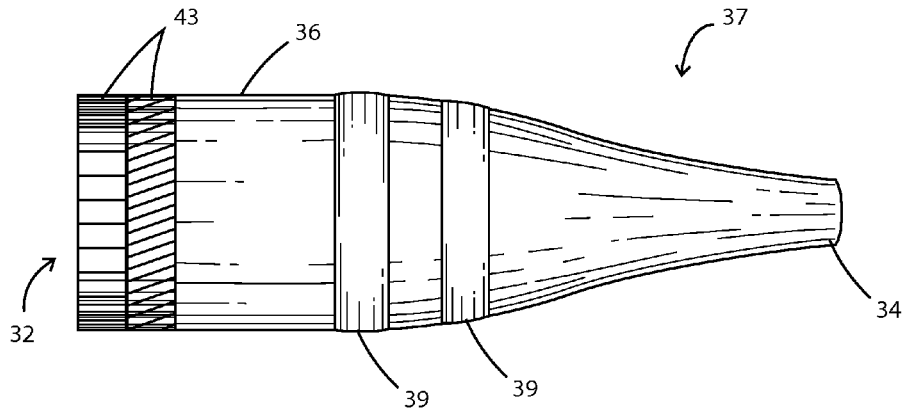
FIGS. 6*a-c* provides a side view of a balloon speculum with two balloon elements.
Figure 6B:
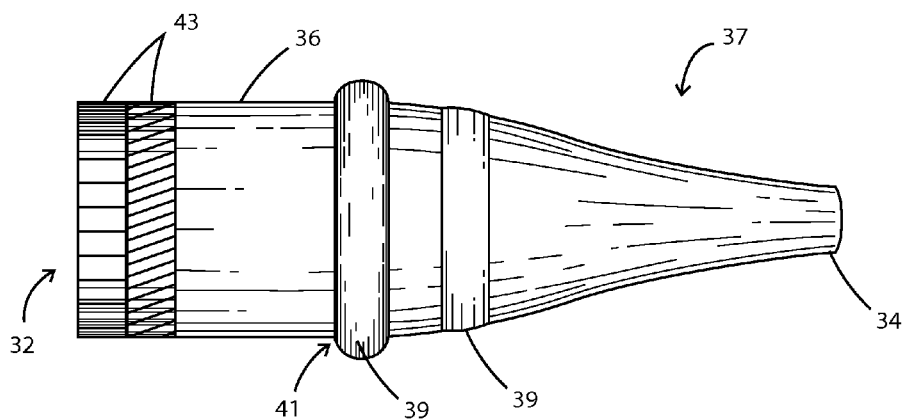
Figure 6C:
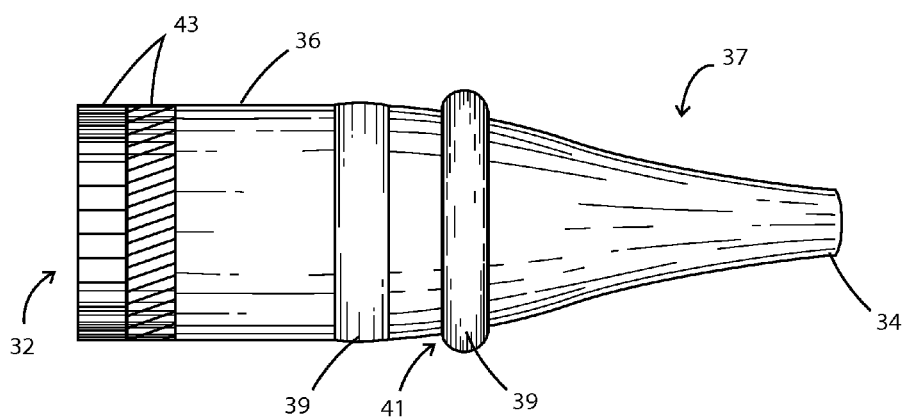

FIGS. 6a-c provides a side view of a balloon speculum 37 comprising a proximate end 32 and a distal end 34, and a speculum body 36 with two balloon elements 39 disposed thereon. While two balloon elements 39 are shown in the Figures, a balloon speculum 37 with only one balloon element 39 can also be used. The balloon elements 39 are housed within grooves 41 along the speculum body 36. The embodiment shown in FIGS. 6a-c are shown with two dials 43, however, one dial or more than two dials can perform the same function. The dials 43 can be rotated clockwise or counter clockwise in order to inflate or deflate either or both of the balloon elements 39 on the speculum. In FIG. 6a, both of the balloon elements 39 are shown as deflated on the balloon speculum 37. FIGS. 6b-6c show the balloon speculum 37 with only one balloon element 39 inflated. When the balloon speculum 37 is not in use, or during the insertion or extraction process of the balloon speculum 37 into and out of the subject, the balloon elements 39 can remain in a deflated state as shown in FIG. 6a. The balloon elements 39 can be placed in an inflated position by manipulation of the dial 43 once the balloon speculum 37 is placed into the subject. In cases where there are more than one balloon element 39 disposed along the speculum body 36 (as shown in FIGS. 6a-c), one balloon element 39 can be inflated at a time.

As used herein, the terms "subject" and "patient" are used interchangeably. As used herein, the term "subject" refers to an animal, preferably a mammal such as a non-primate (e.g., cows, pigs, horses, cats, dogs, rats etc.) and a primate (e.g., monkey and human), and most preferably a human.

It should be borne in mind that all patents, patent applications, patent publications, technical publications, scientific publications, and other references referenced herein are hereby incorporated by reference in this application in order to more fully describe the state of the art to which the present invention pertains.

It is important to an understanding of the present invention to note that all technical and scientific terms used herein, unless defined herein, are intended to have the same meaning as commonly understood by one of ordinary skill in the art. The techniques employed herein are also those that are known to one of ordinary skill in the art, unless stated otherwise. For purposes of more clearly facilitating an understanding the invention as disclosed and claimed herein, the following definitions are provided.

While a number of embodiments of the present invention have been shown and described herein in the present context, such embodiments are provided by way of example only, and not of limitation. Numerous variations, changes and substitutions will occur to those of skill in the art without materially departing from the invention herein. For example, the present invention need not be limited to best mode disclosed herein, since other applications can equally benefit from the teachings of the present invention. Also, in the claims, means-plus-function and step-plus-function clauses are intended to cover the structures and acts, respectively, described herein as performing the recited function and not only structural equivalents or act equivalents, but also equivalent structures or equivalent acts, respectively. Accordingly, all such modifications are intended to be included within the scope of this invention as defined in the following claims, in accordance with relevant law as to their interpretation.

What is claimed is:

1. A multifunctional medical examination instrument comprising:
    an elongated body having a first end and a second end;
    a light emitting member disposed at said first end of said elongated body;
    a power supply associated with said elongated body, said power supply in electrical communication with said light emitting member;
    an otoscope attachment selectively connectable via an otoscope base fitting to said first end of said elongated body over said light emitting member, said otoscope attachment comprising a first end and a second end, wherein said second end comprises a viewing end comprising a magnifying lens, a mirror disposed in said otoscope attachment to reflect light from said light emitting member through said magnifying lens in said viewing end; and
    an adjustable speculum said adjustable speculum comprising a proximal end and a distal end, wherein said proximal end is removably attached to the first end of the otoscope attachment, and said distal end is configured for penetration into an orifice of a subject, said adjustable speculum further comprising a speculum body extending between said proximal and distal ends, the speculum body comprises at least one notch disposed thereon, and wherein a bumper is located on either side of said at least one notch, said adjustable speculum comprising at least one adjustable flange disposed on the speculum body, said adjustable flange may be positioned at any point along the speculum body between the proximate and the distal end, wherein said adjustable flange may be removably received within said at least one notch, and said adjustable flange limits the penetration of the distal end of the speculum into the orifice and provides adjustability of the operable length of the speculum.

2. The medical examination instrument of claim 1, further comprising an Input/Output (I/O) connector projecting out of said second end of said elongated body, said I/O connector in electrical communication with said power supply, wherein said power supply is a rechargeable power supply, and said I/O connector is adapted for operative connection with an external power supply, so as to charge said rechargeable power supply.

3. The medical examination instrument of claim 1, wherein said power supply includes primary batteries and/or corded power.

4. The medical examination instrument of claim 1, wherein said speculum ranges from 10 to 40 millimeters in length.

5. The medical examination instrument of claim 1, wherein said speculum comprises a fixed speculum, comprising a proximate end and a distal end, and a speculum body there between, wherein a flange is fixed at a predetermined position on said speculum body.

6. The medical examination instrument of claim 5, wherein said predetermined position is based on a depth of the orifice of the subject.

7. The speculum of claim 1, wherein said at least one notch includes a marking such that a user of the instrument can identify the at least one notch along the speculum body which correlates with an age group of subjects, such that when the flange is placed within the notch, the speculum penetrates the orifice of the subject to the desired degree.

8. A multifunctional medical examination instrument comprising:
    an elongated body having a first end and a second end;
    a light emitting member disposed at said first end of said elongated body;
    a power supply associated with said elongated body, said power supply in electrical communication with said light emitting member;
    an otoscope attachment selectively connectable via an otoscope base fitting to said first end of said elongated body over said light emitting member, said otoscope attachment comprising a first end and a second end, wherein said second end comprises a viewing end comprising a magnifying lens, a mirror disposed in said otoscope attachment to reflect light from said light emitting member through said magnifying lens in said viewing end; and
    a speculum removably attached to the first end of the otoscope attachment, said speculum comprising at least one flange disposed thereon, wherein the speculum is a bulb speculum, comprising a proximate end, a distal end, and a speculum body extending from said proximate end to said distal end, said proximate end configured to attach to the first end of the otoscope attachment, and said distal end configured for penetration into an orifice of a subject, said bulb speculum formed of a flexible material, and further comprising a dial disposed at said proximal end, said dial adapted to adjust a length of said bulb speculum, such that when said dial is turned in a first direction, the proximate end is moved toward the distal end of the bulb speculum and the at least one flange is formed, said flange comprising a bulb shape in the speculum body between the proximate and distal end of the speculum body, and when said dial is turned in a second direction, the proximate end is moved away from the distal end and the bulb shape is removed.

9. The medical examination instrument of claim 1, wherein said orifice comprises a nostril, an eye, an oral canal, an aural canal, an anus, a urethra, a vagina, or a navel.

10. A speculum configured for attachment to an otoscope attachment of a medical examination instrument, said speculum comprising:
a proximate end, a distal end, and a speculum body extending from said proximate end to said distal end, said proximate end configured for attachment to a first end of the otoscope attachment, and said distal end configured for penetration into an orifice of a subject, said body comprising at least one notch disposed thereon, and wherein a bumper is located on either side of said at least one notch, said speculum further comprising at least one adjustable flange, wherein said at least one adjustable flange is adjustably positioned on the speculum body, removably receivable within sad at least one notch between the proximate end and the distal end of the speculum body, to limit a depth of the penetration of the speculum in the orifice.

11. The adjustable speculum of claim 10, wherein the length of the speculum body ranges from 10 to 40 millimeters.

12. An otoscope kit, comprising:
an elongated body having a first end and a second end;
a light emitting member disposed at said first end of said elongated body;
a rechargeable power supply disposed within said elongated body, said rechargeable power supply in electrical communication with said light emitting member;
an Input/Output (I/O) connector projecting out of said second end of said elongated body, said I/O connector in electrical communication with said rechargeable power supply and adapted for operative connection with an external power supply, so as to charge said rechargeable power supply;
an otoscope attachment selectively connectable via an otoscope base fitting to said first end of said elongated body over said light emitting member, said otoscope attachment comprising a first end and a second end, wherein said second end comprises a viewing end comprising a magnifying lens, a mirror disposed in said otoscope attachment to reflect light form said light emitting member through said magnifying lens in said viewing end; and
at least one adjustable speculum, said adjustable speculum comprising a proximal end and a distal end, said proximal end is configured to attach to the first end of the otoscope attachment, and said distal end is configured for penetration into an orifice of a subject, said speculum further comprising a speculum body extending between said proximal and distal ends, the speculum body comprises at least one notch disposed thereon, and wherein a bumper is located on either side of said at least one notch, said adjustable speculum comprising at least one adjustable flange disposed on the speculum body, said adjustable flange may be positioned at any point along the speculum body between the proximate and the distal end, wherein said adjustable flange may be removably received within said at least one notch, and wherein said flange limits the penetration of the distal end of the speculum into the orifice and is movable along the length of the speculum body so as to provide adjustability of the operable length of the speculum.

13. The otoscope kit of claim 12, wherein the at least one speculum is disposable.

* * * * *